United States Patent [19]

Jegham et al.

[11] Patent Number: 5,418,241

[45] Date of Patent: May 23, 1995

[54] PIPERIDINE DERIVATIVES, THEIR PREPARATION AND THEIR APPLICATION IN THERAPEUTICS

[75] Inventors: Samir Jegham, Argenteuil; Gérard Defosse, Paris; Thomas Purcell, Montfort L'Amaury, all of France

[73] Assignee: Synthelabo, Le Plessis Robinson, France

[21] Appl. No.: 127,058

[22] Filed: Sep. 27, 1993

[30] Foreign Application Priority Data

Sep. 28, 1992 [FR] France .................. 92 11550

[51] Int. Cl.⁶ .................. A61K 31/445; C07D 401/14
[52] U.S. Cl. .................. 514/322; 546/199
[58] Field of Search .................. 546/199; 514/322

[56] References Cited

U.S. PATENT DOCUMENTS

| | | | |
|---|---|---|---|
| 5,008,390 | 4/1991 | Bender | 546/199 |
| 5,192,775 | 3/1993 | Malen | 514/321 |
| 5,280,030 | 1/1994 | Jegham | 514/322 |

FOREIGN PATENT DOCUMENTS 0197840 10/1986 European Pat. Off. .
0494010 7/1992 European Pat. Off. .

OTHER PUBLICATIONS

C. A. Lipinski et al., "Bioisoteric prototype design . . . ", vol. 29, No. 11, Nov. 1986, Journal of Medicinal Chemistry, Washington, USA.
W. Schunack, vol. 306, No. 12, Dec. 1973, Archiv der Pharmazie, Weinheim, Germany.

Hayashi et al "5HT₃ Receptor Antagonists" J. Med. Chem. 35 4893-4902 (1992).
Glennon "Central Serotonin Receptors as Target for Drug Research" J. Med. Chem. 30 1-12 (1967).

*Primary Examiner*—Celia Chang
*Attorney, Agent, or Firm*—Jacobson, Price, Holman & Stern

[57] ABSTRACT

The invention provides a compound which is a piperidine derivative of formula (I)

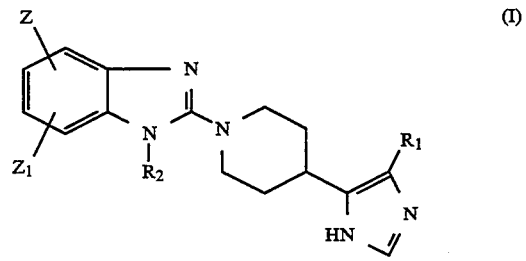

in which
$R_1$ is hydrogen or straight or branched ($C_1$-$C_6$) alkyl, $R_2$ is hydrogen or straight or branched ($C_1$-$C_8$) alkyl, Z and $Z_1$ which may be the same or different, each is hydrogen, chlorine, hydroxyl, amino, nitro, hydroxymethyl, ($C_1$-$C_2$) alkyl, ($C_1$-$C_8$) alkoxy straight or branched ($C_1$-$C_5$) alkoxycarbonyl or aryl ($C_1$-$C_2$) alkoxy, Z is in position 4, 6 or 7 and Z and $Z_1$ cannot both be hydrogen, or its addition salt with a pharmaceutically acceptable acid and its therapeutic application.

5 Claims, No Drawings

PIPERIDINE DERIVATIVES, THEIR PREPARATION AND THEIR APPLICATION IN THERAPEUTICS

The present invention relates to piperidine derivatives, their preparation and their application in therapeutics.

The compounds of the invention are piperidine derivatives of formula (I)

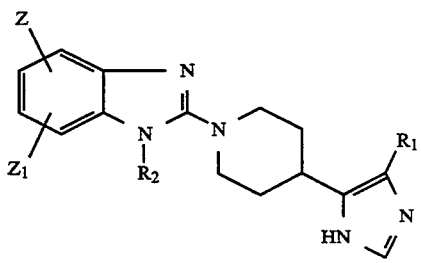

in which $R_1$ is hydrogen or straight or branched ($C_1$–$C_6$) alkyl, $R_2$ is hydrogen or straight or branched ($C_1$–$C_8$) alkyl, Z and $Z_1$ which may be the same or different, each is hydrogen, chlorine, hydroxyl, amino, nitro, hydroxymethyl, ($C_1$–$C_3$) alkyl, ($C_1$–$C_8$) alkoxy straight or branched ($C_1$–$C_5$)alkoxycarbonyl or aryl ($C_1$–$C_2$) alkoxy, Z is in position 4, 6 or 7 and Z and $Z_1$ cannot both be hydrogen, or its addition salt with a pharmaceutically acceptable acid.

The alkyl and aloxy groups may be branched or straight chain groups. A, $C_1$ to $C_6$ or $C_1$ to $C_8$ alkyl group is preferbly a $C_1$ to $C_4$ alkyl group eg. methyl, ethyl, propyl, isopropyl, butyl, sec. butyl or tert butyl, more preferably methyl or ethyl.

A $C_1$ to $C_8$ alkoxy group is preferably a $C_1$ to $C_4$ alkoxy group, eg. methoxy, ethoxy, propoxy, isopropoxy, butoxy or tert butoxy, more preferably it is methoxy or ethoxy.

Preferably $R_1$ is hydrogen, methyl or ethyl. Preferably $R_2$ is hydrogen, methyl, ethyl, n-propyl or isopropyl. Preferably Z is chlorine, hydroxyl, hydroxymethyl or methyl.

Preferably the pharmaceutically acceptable acid with which the addition salt is formed is hydrochloric acid, fumaric acid or maleic acid.

According to the invention, the preferred compounds are the compounds of formula (I) are those in which Z is in position 7.

Amoung these compounds, the particularly preferred compounds are those where $Z_1$ is chlorine or hydrogen.

The compounds of the invention can exist in the form of free bases or of addition salts with pharmaceutically acceptable of the formula (I) form part of the invention.

In accordance with the invention, it is possible to prepare the compounds of formula (I) according to the process illustrated in Scheme 1.

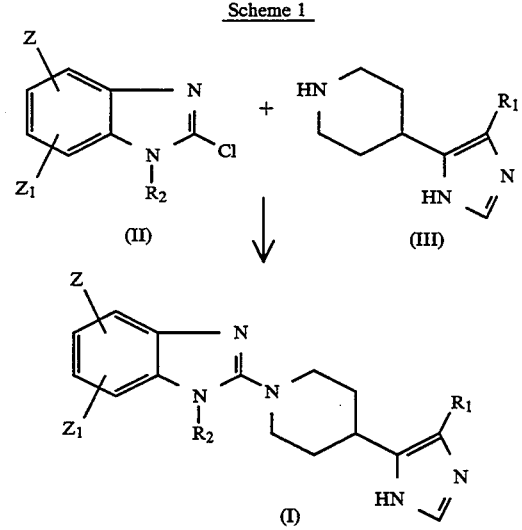

Scheme 1

A benzimidazole derivative of formula (II), in which $R_2$, Z and $Z_1$ are as defined above, is reacted with a piperidine derivative of formula (III), in which $R_1$ is as defined above. The reaction is carried out in a solvent such as, for example, isopentyl alcohol. The compounds of formula (I) in which $Z_1$ represents an amino group are obtained from compounds of formula (I) in which $Z_1$ represents a nitro group, according to techniques described in the literature or known to one skilled in the art.

The compounds of formula (I) in which Z or $Z_1$ represents a hydroxyl group are obtained respectively from compounds of formula (I) in which Z or $Z_1$ represents a methoxy group, according to techniques described in the literature or known to one skilled in the art.

Compounds of formula (I) in which Z or $Z_1$ represents a hydroxymethyl group are obtained respectively from compounds of formula (I) in which Z or $Z_1$ represents an alkoxycarbonyl group, according to techniques described in the literature or known to one skilled in the art.

Starting compounds are available commercially or are described in the literature or can be prepared according to methods which are described therein or which are known to one skilled in the art.

2-Chloro-3-nitrophenol is prepared according to the technique described in *J. Prakt. Chem.*, 1930, 127, 20.

2-Chloro-4(7)-methoxybenzimidazole is prepared according to the technique described in *Chemical Abstract*, 67: 108597x.

Ethyl 2-[[(1,1-dimethylethoxy)carbonyl]amino]-3-nitrobenzoate is prepared according to the technique described in European Patent 0,459,136.

4-Chloro-5-nitro-1,2-benzenediamine is described in *Heterocycle*, 1987, 26, No. 9, 2433.

The compounds of formula (II) were prepared according to protocols similar to those described in *J. Med. Chem.*, 1986, 29, 1178–83 and in European Patent No. 0,039,190.

4-(1H-Imidazole-4-yl)piperidine is described in *Arch. Pharmaz.*, (Weinheim. Ger.) 1973, 306 (12), 934–42 and in European Patent Application 0,197,840.

4-(5-Methyl-1H-imidazole-4-yl)pyridine is described in *J. Med. Chem.*, 1986, 29, 2154–63.

Examples 1 to 4 which follow illustrate the preparation of a number of compounds of formula (II).

Examples 5 to 9 which follow illustrate in detail the preparation of the compounds according to the invention.

The microanalysis and the IR and NMR spectra confirm the structure of the compounds obtained.

EXAMPLE 1

2-Chloro-1-(1-methylethyl)-7-phenylmethoxy-1H-benzimidazole 1.1. 2-Chloro-3-nitrophenol 73 g (0.52 mol) of 3-nitrophenol are dissolved in 2 liters of 6N hydrochloric acid while heating. The mixture is cooled in an ice bath to 28°–30° C. 32 g (0.26 mol) of potassium chlorate in 500 ml of water are added over 1.5 hours and then, at the end of the addition, the mixture is left stirring for 30 minutes at 28°–30° C. The mixture is cooled to 15° C. and 1 liter of dichloromethane is added. The layers are separated and the organic phase is washed with water. The organic phase is dried and evaporated. The residue is purified by chromatography on a column of silica gel, eluting with a dichloromethane/methanol (80/20) mixture. Recrystallization is carried out from toluene. 29 g of product are obtained.

Melting point=130° C. Yield=32%

1.2. 2-Chloro-1-nitro-3-(phenylmethoxy)benzene 1.43 g (0.036 mol) of a 60% sodium hydride as a solution are placed in 25 ml of dimethylformamide in a 250 ml, three-necked, round-bottomed flask. 6 g of the chlorinated derivative obtained in 1.1 are added at room temperature and then 6.6 g (0.039 mol) of (bromomethyl)benzene are added dropwise. The mixture is left stirring for 24 hours at room temperature. The reaction mixture is thrown onto a mixture of ice-cold water and hexane, and the product is drained off, washed with a mixture of ice-cold water and hexane and then dried, at 60° C., under vacuum. 8.4 g of product are obtained.

Melting point=94° C. Yield=92%

1.3. N-(1-Methylethyl)-2-nitro-6-(phenylmethoxy)benzeneamine 8.4 g (0.032 mol) of the chlorinated derivative obtained above in 1.2 are placed in 20 ml of isopropylamine and the mixture is heated in an autoclave at 110° C. for 18 hours using an oil bath. The excess amine is evaporated and the residue is taken up in a mixture of water and ether. The organic phase is collected, washed with water, dried and evaporated. 8.2 g of product are obtained.

Yield=90%

1.4. N²-(1-methylethyl)-3-(phenylmethoxy)-1,2-benzenediamine 100 mg (0.44 mol) of platinum oxide are placed in 25 ml of ethanol in a 250 ml Parr flask. Hydrogenation is carried out for 15 minutes, under pressure of 15 psi, and then 0.5 g (0.0017 mol) of the nitro derivative obtained above in 1.3 is added. The mixture is left for 5 minutes, the catalyst is filtered and the solvent is evaporated. The residue is taken up in ether and is washed successively with 1N sodium hydroxide solution and with water. The organic phase is dried and evaporated.

Yield=92%

1.5. 1-(1-Methylethyl)-7-(phenylmethoxy)-1,3-dihydro-2H-benzimidazole-2-one

A mixture of 2.2 g (0.036 mol) of urea and 6.6 g (0.026 mol) of the diamine obtained above in 1.4 is heated at 175°–180° C. for 2 hours. The residue is taken up in a mixture of water and ether and then evaporated. The final gummy residue is taken up in ether and filtered. 4.6 g of product are obtained.

Melting point=224° C. Yield=64%

1.6. 2-Chloro-1-(methylethyl)-7-phenylmethoxy-1H-benzimidazole 4 g (0.014 mol) of the compound obtained above in 1.5 are heated at reflux for 1.5 hours in 50 ml of phosphoryl chloride. The solvent is evaporated, the residue is cooled to 0° C. and basified with a water/aqueous ammonia mixture to a pH of 8. Extraction is carried out with an ether/dichloromethane mixture, and the extract is dried and evaporated. The residue is purified by chromatography on a column of silica gel, eluting with a methanol/dichloromethane (2/98) mixture. 2 g of product are obtained.

Yield=48%

EXAMPLE 2

2-Chloro-4(7)-methoxy-1-(1-methylethyl)-1H-benzimidazole

Route 1

3.74 g (0.031 mol) of 2-bromopropane are added to a mixture of 5.3 g (0.029 mol) of 2-chloro-4(7)-methoxy-1H-benzimidazole in 30 ml of dimethyl sulphoxide and of 4.41 g (0.032 mol) of potassium carbonate and the mixture is then heated for 3 hours at 60° C. The reaction mixture is poured onto water, extracted with ether and washed successively with water and with a saturated sodium chloride solution. The organic phase is dried, filtered and evaporated. The crude residue obtained is purified by chromatography on a column of silica gel, eluting with a cyclohexane/ethyl acetate (4/1) mixture. 2.5 g of 2-chloro-4-methoxy-1-(1-methylethyl)-1H-benzimidazole (A) and 2.5 g of 2-chloro-7-methoxy-1-(1-methylethyl)-1H-benzimidazole (B) are obtained.

A: Melting point=99°–101° C. Yield=40%
B: Melting point=63° C. Yield=40%

Route 2

2-Chloro-7-methoxy-1-(1-methylethyl)-1H -benzimidazole is prepared according to the method described in Example 1 from 2-chloro-1-methoxy-3-nitrobenzene.

Melting point=63° C. Yield=44%

EXAMPLE 3

Ethyl 2-Chloro-1-(1-methylethyl)-1H-benzimidazole-7-carboxylate 3.1. Ethyl 2-[(1-methylethyl)amino]-3-nitrobenzoate 4.8 g (0.12 mol) of a 60% sodium hydride solution are added, at 0° C., under argon, and in portions, to a solution of 34 g (0.11 mol) of ethyl 2-[[(1,1-dimethylethoxy)carbonyl]amino]-3-nitrobenzoate in 100 ml of dimethylformamide. The mixture is left stirring for 20 minutes at 0° C. 55.9 g (0.33 mol) of 2-iodopropane are then added and the mixture is heated at 80° C. for 4 hours and then at room temperature for 48 hours. Hydrolysis is carried out by adding water and extraction is carried out 3 times with ethyl acetate. The organic phase is collected and washed successively with water and with a saturated sodium chloride solution. It is dried and evaporated.

3.2. Ethyl 3-Amino-2-[(1-methylethyl)amino]benzoate

A solution of 27 g (0.011 mol) of the nitro derivative obtained above in 3.1 in 250 ml of ethyl acetate is hydrogenated at 45° C. for 5 hours at ordinary pressure in the presence of 2.7 g of 10% palladium-on-charcoal. The catalyst is filtered, the solvent is evaporated and the residue is purified by chromatography on a column of silica gel, eluting with a hexane/ethyl acetate (9/1) mixture. The product is obtained in the form of an oil.

3.3. Ethyl 1-(1-methylethyl)-2-oxo-2,3-dihydro-1H-benzimidazole-7-carboxylate

A mixture of 5 g (0.023 mol) of the diamine obtained above in 3.2 and 4 g (0.066 mol) of urea is heated at 180° C. for 8 hours. The residue is taken up in ether and filtered.

Yield=60%

3.4. Ethyl 2-chloro-1-(1-methylethyl)-1H-benzimidazole-7-carboxylate 3.2 g (0.013 mol) of the benzimidazolone obtained above in 3.3 is heated at reflux for 20 hours in 25 ml of phosphoryl chloride. The phosphoryl chloride is evaporated, the residue is basified to a pH of 8 with aqueous ammonia and extraction is carried out with ethyl acetate. The organic phase is collected, evaporated and dried. Purification is carried out by chromatography on a column of silica gel, eluting with a dichloromethane/methanol (95/5) mixture.

EXAMPLE 4

2,5-Dichloro-6-nitro-1H-benzimidazole 4.1. 5-Chloro-6-nitro-1,3-dihydro-2H-benzimidazole-2-one A mixture of 14 g (0.074 mol) of 4-chloro-5-nitro-1,2-benzenediamine and of 13.44 g (0.226 mol) of urea is heated at 180° C. for 4 hours. The reaction mixture is cooled and evaporated to dryness. The residue is taken up in methanol and evaporated again. The residue is triturated in ether and a solid is obtained which is filtered. The product is used as is in the subsequent stages.

4.2. 2,5-Dichloro-6-nitro-1H-benzimidazole

It is prepared according to the method described in Example 1.6 from the benzimidazolone obtained above in 4.1.

Yield=32%

EXAMPLE 5

2-[4-(1H-imidazole-4-yl)piperidine-1-yl]-1-(1-methylethyl)-7-(phenylmethoxy)-1H-benzimidazole maleate A mixture of 1 g (0.0066 mol) of 4-(1H-imidazole-4-yl)piperidine and of 1 g (0.0033 mol) of the chloro derivative prepared according to the method described in Example 1.6 is heated for 48 hours at 120° C. in 4 ml of isopentyl alcohol. The solvent is evaporated and the residue is taken up in a mixture of water and dichloromethane. The layers are separated, the organic phase is collected, evaporated and dried. The residue is purified by chromatography on a column of silica gel, eluting with a dichloromethane/methanol/aqueous ammonia (45/5/0.5) mixture. 0.9 g of pure product is obtained.

Yield=73%

The maleate is prepared in acetone. The product is dissolved in the base form in acetone, one equivalent of an alcohol solution of maleic acid is added, stirring is carried out, evaporation is carried out and the product is recrystallized, in the maleate form, from acetone.

Melting point=158°-159° C.

EXAMPLE 6

2-[4-(1H-imidazole-4-yl)piperidine-1-yl]-7-methoxy-1-(1-methylethyl)-1H-benzimidazole A mixture of 1.34 g (0.009 mol) of 4-(1H-imidazole-4-yl)piperidine and of 1 g (0.0045 mol) of the chloro derivative prepared according to the method described in Example 2 is heated for 96 hours at 120° C. in 4 ml of isopentyl alcohol. The solvent is evaporated and the residue is taken up in a mixture of water and ether. The layers are separated, the organic phase is recovered, washed with water and ether, evaporated and dried. The residue is purified by chromatography on a column of silica gel, eluting with a dichloromethane/methanol/aqueous ammonia (45/5/0.5) mixture. 1 g of pure product is obtained which is recrystallized from a mixture containing dichloromethane, methanol and ether. 0.9 g of product is obtained.

Melting point=250°-253° C. Yield=60%

EXAMPLE 7

Ethyl 2-[4-(1H-imidazole-4-yl)piperidine-1-yl]-1-(1methylethyl)-1H-benzimidazole-7-carboxylate The chloro derivative obtained above in 3.4 is reacted with 4-(1H-imidazole-4-yl)piperidine according to the method described above in Example 5.

The fumarate is prepared in ethanol by adding one equivalent of a fumaric acid solution. After stirring and evaporation, the fumarate is recrystallized from ethanol.

Melting point=163°-165° C. Yield=53%

EXAMPLE 8

7-Hydroxymethyl-2-[4-(1H-imidazole-4-yl)piperidine-1yl]-1-(1-methylethyl)-1H-benzimidazole 10 ml of a 1M solution of diisobutylaluminium hydride in tetrahydrofuran are added to a solution of 0.6 g (0.002 mol) of ester, prepared according to the method described in Example 7, in 10 ml of tetrahydrofuran, at 0° C. The mixture is left to return, with stirring, to room temperature and the mixture is kept stirring for 24 hours. A mixture of tetrahydrofuran and water is added, filtration is carried out, washing is carried out with dichloromethane and the solvent is evaporated. The residue is purified by chromatography on a column of silica gel, eluting with a dichloromethane/methanol (8/2) mixture.

The fumarate is prepared as described in Example 7.

Melting point=186°-193° C. (dec.) Yield=45%

EXAMPLE 9

2-[4-(5-methyl-1H-imidazole-4-yl)piperidine-1-yl]-5-chloro-6-nitro-1H-benzimidazole The chloro derivative obtained according to the method described in Example 4.2 is reacted with 4-(5-methyl-1H-imidazole-4-yl)piperidine under the conditions described in Example 5.

Melting point=>250° C. Yield=40%

The following table illustrates the chemical structures and the physical properties of a number of compounds according to the invention.

Legend of the table in the "M.p. (°C.)" column of the table (dec.) means decomposition in the "Salt" column of the table (x:y) means x mol of acid per y mol of base,
the absence of any mention means that a compound is in the base form,
chlor. represents the hydrochloride,
fum. represents the fumarate,
mal. represents the maleate.

the presence of 0.1 μM of paroxetine and of 1 μM of ketanserin. The non-specific bonding is determined in the presence of 1 μM of ondansetron. After incubating, the tested mixture is diluted with 5 ml of ice-cold 50 mM Tris-HCl buffer (pH=7.4 at 0° C.). The membranes are collected by filtration on Whatman GF/B ™ filters pretreated with 0.05% of polyethyleneimine and they are washed with three volumes of 5 ml of ice-cold 50

TABLE (I)

| No. | $R_1$ | $R_2$ | Z | $Z_1$ | M.p. (°C.) | Salt |
|---|---|---|---|---|---|---|
| 1 | —H | —CH(CH$_3$)$_2$ | 7-Cl | —H | 195–197 | fum. (1:1) |
| 2 | —H | —CH(CH$_3$)$_2$ | 7-OH | —H | 174–180 | — |
| 3 | —H | —CH(CH$_3$)$_2$ | 4-OH | —H | 264–265 | — |
| 4 | —H | —CH(CH$_3$)$_2$ | 7-CH$_2$OH | —H | 186–193 (dec.) | fum. (1:1) |
| 5 | —H | —CH(CH$_3$)$_2$ | 7-CH$_3$ | —H | 178–180 | fum. (1:1) |
| 6 | —H | —CH(CH$_3$)$_2$ | 4-CH$_3$ | —H | 180–185 | fum. (1:1) |
| 7 | —H | —CH(CH$_3$)$_2$ | 4-OCH$_3$ | —H | 105–110 | — |
| 8 | —H | —CH(CH$_3$)$_2$ | 7-OCH$_3$ | —H | 250–253 | — |
| 9 | —H | —CH(CH$_3$)$_2$ | 7-OC$_8$H$_{17}$ | —H | 147 | mal. (2:1) |
| 10 | —H | —CH(CH$_3$)$_2$ | 7-OCH$_2$C$_6$H$_5$ | —H | 158–159 | mal. (2:1) |
| 11 | —H | —CH(CH$_3$)$_2$ | 7-COOC$_2$H$_5$ | —H | 163–165 | fum. (1:1) |
| 12 | —CH$_3$ | —CH(CH$_3$)$_2$ | 7-Cl | —H | 192–195 | fum. (1:1) |
| 13 | —CH$_3$ | —CH(CH$_3$)$_2$ | 4-OCH$_3$ | —H | 111–119 | — |
| 14 | —CH$_3$ | —CH(CH$_3$)$_2$ | 7-OCH$_3$ | —H | 273–275 | — |
| 15 | —CH$_3$ | —CH(CH$_3$)$_2$ | 7-OC$_8$H$_{17}$ | —H | 136–138 | — |
| 16 | —CH$_3$ | —CH(CH$_3$)$_2$ | 7-COO(CH$_2$)$_2$CH(CH$_3$)$_2$ | —H | 188–190 | fum. (1:1) |
| 17 | —CH$_3$ | —CH(CH$_3$)$_2$ | 7-OCH$_2$C$_6$H$_5$ | —H | 170–172 | fum. (3.2) |
| 18 | —CH$_3$ | —H | 6-NO$_2$ | 5-Cl | >250 | — |
| 19 | —CH$_3$ | —H | 6-NH$_2$ | 5-Cl | >300 | chlor. (2:1) |

The compounds of the invention have formed the subject of pharmacological tests which have shown their advantage as therapeutically active substances.

Thus, they were tested for their inhibiting effects on the binding of [$^3$H] quipazine with serotoninergic receptors of 5-HT$_3$ type present in the cerebral cortex of rats, according to a variant of the method described by Milburn and Peroutka (J. Neurochem., 52, 1787–1792, 1989).

Male Sprague-Dawley rats, from 150 to 200 g, are used in all the tests. The cerebral cortex is removed from them and is homogenized in 20 volumes (weight-/volume) of 25 mM Hepes buffer or of 25 mM Hepes buffer containing sodium chloride (180 mM), calcium chloride (2.5 mM), potassium chloride (5 mM) and magnesium chloride (1.2 mM) (pH=7.4) using a Polytron ™ grinder. After centrifuging the suspension for 10 min at 45,000×g, the pellet is resuspended in the initial volume of buffer, optionally containing 0.05% of Triton X-100 ™ and a first incubation is carried out for 30 min at 37° C. A further two centrifugations are then carried out as described above and the final pellet is taken up in 11.7 volumes of 25 mM Hepes buffer at pH=7.4.

The bonding of [$^3$H] quipazine (51.6–69.8 Ci/mmol, New England Nuclear, Boston, Mass., USA) is determined by incubating 150 μl of the membrane suspension with the radio ligand (0.8 nM) in a final volume of 1 ml for 30 min at 25° C. in the absence or in the presence of the compound to be studied. Incubation takes place in mM Tris-HCl buffer.

The radioactivity retained on the filters is measured by liquid scintillation spectrometry at an efficiency of 50 to 60%.

The results are expressed as the concentration (IC$_{50}$) of the studied compound which inhibits 50% of the bonding of [$^3$H] quipazine, determined by a graphic or mathematical method. The most active compounds of the invention in this test are characterized by IC$_{50}$ values which are less than 1 nM ($10^{-9}$M).

The compounds of the invention were also tested for their effect on the Bezold-Jarisch reflex, that is to say an intense bradycardia, caused by intravenous injection of serotonin. This reflex brings into play the stimulation of the specific 5-HT$_3$ receptors of the vagus, which causes a depolarization and thus a secretion of acetylcholine, which is the natural vagal neurotransmitter.

Male Sprague-Dawley rats are anaesthetized with urethane (1 to 25 g/kg intraperitoneally), the blood pressure is measured by virtue of a catheter placed in the carotid artery and pressure impulses are used to activate a cardiotachometer. Cannulae are placed in the two femoral veins in order to facilitate the intravenous administration of the products.

The dose/response curves of the bradycardia caused by the injection of doses of 30 μg/kg of serotonin, before and after the injection of the compounds to be studied, are traced.

The most active compounds of the invention in this test inhibit the bradycardia caused by the serotonin by at least 50% with a dose of 10 μg/kg administered intravenously.

The compounds of the invention were also studied for their effects on emesis in ferrets (male, 1 to 1.4 kg), according to a method described by Costall et al. (*Neuropharmacology* 25(8), 959–961, 1986).

The compounds to be studied or physiological serum are administered intravenously (jugular vein), under halothane anaesthesia, immediately before an intravenous perfusion of cisplatin (10 mg/kg in 10 min).

The animals are then observed for 3 h, noting the number of emetic crises, the total number of spasms and of vomitings, as well as the time period for the appearance of the first crisis.

The most active compounds of the invention in this test show an anti-emetic effect after administration of a dose of less than 5 mg/kg orally.

Finally, the compounds of the invention were studied for their effects on the atypical 5-HT receptors (5-HT$_4$) in the ileum of the guinea pig, after Craig and Clarke, *J. Pharm. Exp. Ther.*, 252 (3), 1378–1386, (1990).

Three-coloured male Jegard guinea pigs, of 300 to 400 g, are killed by a blow to the head and exsanguinated. An approximately 3 cm fragment of ileum is rapidly removed from the ileo-coecal junction and is washed with 10 ml of tepid Krebs buffer (composition in mM: NaCl=118; CaCl$_2$=2.6; KCl=4.9; NaH$_2$PO$_4$=1; MgSO$_4$=1.2; NaHCO$_3$=25; glucose=11.7). The ileum is mounted on a 2 ml pipette and the longitudinal muscle is carefully separated with dental cotton impregnated with Krebbs buffer. The organ is connected to an isometric transducer under a basal tension of 0.5 g and maintained in a Krebs bath at 37° C. aerated with a carbogen stream. After leaving for approximately 30 min, an electrical stimulation (0.2 Hz, 1.5 ms, supramaximal voltage ≦45 V) is applied by virtue of H. Sachs, model F2H, field electrodes connected to a Grass S88 TM stimulator, until the contractions (or "twitches") have stabilized. $3 \times 10^{-7}$M of phenoxybenzamine is then added to the bath and this reduces the amplitude of the contractions by up to approximately 50% (≦30 min). The organ is then washed six times at intervals of 5 min. Before the fourth washing, serotonin ($3 \times 10^{-7}$M) is added. If necessary, the amplitude of the contractions is reduced to 50% of the supramaximal amplitude by reducing the electrical voltage after the sixth washing. The concentration/effect curve is constructed by cumulative additions, at intervals of 1 min, of the compound to be studied.

The responses are measured in terms of the ability to restore the amplitude of the contractions to the level of that obtained by virtue of the supramaximal voltage and after treatment with phenoxybenzamine.

The compounds of the invention behave as agonists, partial agonists or antagonists of the said receptors, some among them being active at concentrations below 10 nM.

The results of the biological tests show that the compounds of the invention are ligands of the serotoninergic receptors. As shown above, they have, in particular, an interaction with the receptors of 5-HT$_3$ and 5-HT$_4$ type.

They can thus be used for the treatment and prevention of disorders in which the serotoninergic receptors are involved, such as nausea and vomiting, for example, following an antitumor treatment or the administration of an anaesthetic; disorders of the central nervous system such as schizophrenia, mania, anxiety and depression; cognitive disorders such as senile dementia or Alzheimer's presenile dementia; dyskinesia, pains, migraines and headaches; disorders of dependence on or weaning from alcohol or drugs; disorders of gastrointestinal action such as dyspepsia, peptic ulcer, heartburn and flatulence; disorders of the cardiovascular system and respiratory disorders.

To this end, they can be presented in any form suitable for oral or parenteral administration, such as tablets, sugar-coated tablets, capsules including hard gelatin capsules, drinkable or injectable suspensions or solutions, and the like, in combination with suitable excipients, and containing doses so as to make possible administration of 0.005 to 5 mg/kg from 1 to 4 times per day.

The present invention further provides a method of medical treatment of the above disorders which comprises administering to the patient an effective amount of a compound of the invention.

We claim:

1. A compound which is a piperidine derivative of formula (I)

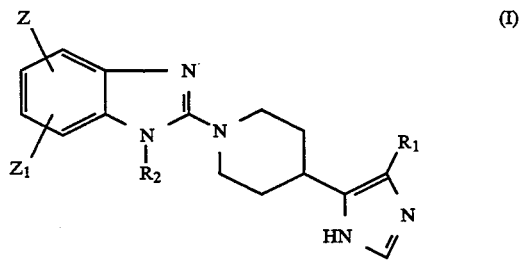

in which

R$_1$ is hydrogen or straight or branched (C$_1$–C$_6$) alkyl,

R$_2$ is hydrogen or straight or branched (C$_1$–C$_8$) alkyl,

Z and Z$_1$ which may be the same or different, each is hydrogen, chlorine, hydroxyl, amino, nitro, hydroxymethyl, (C$_1$–C$_2$) alkyl, (C$_1$–C$_8$) alkoxy, straight or branched (C$_1$–C$_5$) alkoxycarbonyl, aryl (C$_1$–C$_2$) alkoxy, except that when one of Z and Z$_1$ is hydrogen, the other cannot be hydrogen, chlorine or (C$_1$–C$_2$) alkyl, and Z is in position, 4, 6 or 7, or an addition salt thereof with a pharmaceutically acceptable acid.

2. A compound according to claim 1, wherein R$_1$ is hydrogen, methyl, or ethyl.

3. A compound according to claim 1, wherein R$_2$ is hydrogen, methyl, ethyl, N-propyl, or isopropyl.

4. A compound according to claim 1, wherein Z is in position 7.

5. 2-[4-(1H-imidazole-4-yl)piperidine-1-yl]-7-methoxy-1-(1-methylethyl)-1H-benzimidazole or an addition salt thereof with a pharmaceutically acceptable acid.

* * * * *